(12) United States Patent
Warner et al.

(10) Patent No.: US 9,096,078 B2
(45) Date of Patent: *Aug. 4, 2015

(54) PROCESS AND APPARATUS FOR PRINTING ASSEMBLED ABSORBENT ARTICLES WITH CUSTOM GRAPHICS

(71) Applicant: The Procter & Gamble Company, Cincinnati, OH (US)

(72) Inventors: Alrick Vincent Warner, Loveland, OH (US); Hui Yang, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 14/505,596

(22) Filed: Oct. 3, 2014

(65) Prior Publication Data

US 2015/0015649 A1 Jan. 15, 2015

Related U.S. Application Data

(63) Continuation of application No. 13/600,298, filed on Aug. 31, 2012, now Pat. No. 8,876,279.

(51) Int. Cl.
*B41J 2/01* (2006.01)
*B41J 11/00* (2006.01)
(Continued)

(52) U.S. Cl.
CPC ....... *B41J 11/0015* (2013.01); *A61F 13/15577* (2013.01); *A61F 13/15731* (2013.01);
(Continued)

(58) Field of Classification Search
CPC .......... B41J 11/007; B41J 11/41; B41J 15/24; B41J 13/103; B41J 13/22; B41J 13/24; B41J 13/28; B41J 13/08; B41J 13/10; B41J 13/12; B41J 13/14; B41J 13/16
USPC ................. 347/4, 9, 14, 16, 19, 101, 104–107
See application file for complete search history.

(56) References Cited

U.S. PATENT DOCUMENTS 3,848,594 A 11/1974 Buell
3,929,135 A 12/1975 Thompson
(Continued)

FOREIGN PATENT DOCUMENTS

EP 0 565 606 B1 10/1993
WO WO 93/25172 12/1993
(Continued)

OTHER PUBLICATIONS

PCT International Search Report, dated Nov. 14, 2013, 9 pages.

*Primary Examiner* — Juanita D Jackson
(74) *Attorney, Agent, or Firm* — Charles R. Matson

(57) ABSTRACT

The present disclosure relates to methods and apparatuses for printing graphics on absorbent articles. Printing systems according to the present disclosure may include a carrier apparatus that transports individual absorbent articles past a printing station, which prints a custom graphic on the absorbent articles. The carrier apparatus may include a hook member connected with an endless belt. The printing system may also include a pressing apparatus positioned adjacent the endless belt. During operation, an absorbent article may be positioned on a hook member, and the endless belt conveys the absorbent article in the machine direction past the printing station. As the absorbent article advances toward the printing station, the pressing apparatus compresses and flattens the absorbent article against the hook member to help provide a relatively flat, smooth surface on the absorbent article to be printed. The printing station then prints a graphic on the advancing article.

10 Claims, 5 Drawing Sheets

(51) Int. Cl.
    *A61F 13/514* (2006.01)
    *A61F 13/15* (2006.01)
    *B41J 3/28* (2006.01)
    *B41J 13/10* (2006.01)

(52) U.S. Cl.
    CPC ..... *A61F 13/15747* (2013.01); *A61F 13/15764* (2013.01); *A61F 13/15804* (2013.01); *A61F 13/51496* (2013.01); *B41J 3/28* (2013.01); *B41J 11/007* (2013.01); *B41J 13/103* (2013.01)

(56) References Cited

U.S. PATENT DOCUMENTS

| | | |
|---|---|---|
| 4,324,246 A | 4/1982 | Mullane et al. |
| 4,342,314 A | 8/1982 | Radel et al. |
| 4,463,045 A | 7/1984 | Ahr et al. |
| 4,609,518 A | 9/1986 | Curro et al. |
| 4,610,678 A | 9/1986 | Weisman et al. |
| 4,629,643 A | 12/1986 | Curro et al. |
| 4,662,875 A | 5/1987 | Hirotsu et al. |
| 4,673,402 A | 6/1987 | Weisman et al. |
| 4,695,278 A | 9/1987 | Lawson |
| 4,795,454 A | 1/1989 | Dragoo |
| 4,834,735 A | 5/1989 | Alemany et al. |
| 4,846,815 A | 7/1989 | Scripps |
| 4,888,231 A | 12/1989 | Angstadt |
| 4,894,060 A | 1/1990 | Nestegard |
| 4,946,527 A | 8/1990 | Battrell |
| 4,968,312 A | 11/1990 | Khan |
| 4,988,344 A | 1/1991 | Reising et al. |
| 4,988,345 A | 1/1991 | Reising |
| 4,990,147 A | 2/1991 | Freeland |
| 5,006,394 A | 4/1991 | Baird |
| 5,062,840 A | 11/1991 | Holt et al. |
| 5,137,537 A | 8/1992 | Herron et al. |
| 5,147,345 A | 9/1992 | Young et al. |
| 5,151,092 A | 9/1992 | Buell et al. |
| 5,171,236 A | 12/1992 | Dreier et al. |
| 5,221,274 A | 6/1993 | Buell et al. |
| 5,260,345 A | 11/1993 | DesMarais et al. |
| 5,269,755 A | 12/1993 | Bodicky |
| 5,306,266 A | 4/1994 | Freeland |
| 5,342,338 A | 8/1994 | Roe |
| 5,387,207 A | 2/1995 | Dyer et al. |
| 5,397,318 A | 3/1995 | Dreier |
| 5,514,121 A | 5/1996 | Roe et al. |
| 5,540,671 A | 7/1996 | Dreier |
| 5,554,142 A | 9/1996 | Dreier et al. |
| 5,562,646 A | 10/1996 | Goldman et al. |
| 5,571,096 A | 11/1996 | Dobrin et al. |
| 5,595,567 A | 1/1997 | King et al. |
| 5,624,427 A | 4/1997 | Bergman et al. |
| 5,650,222 A | 7/1997 | DesMarais et al. |
| 5,653,703 A | 8/1997 | Roe et al. |
| 5,669,894 A | 9/1997 | Goldman et al. |
| 5,735,840 A | 4/1998 | Kline et al. |
| 5,865,823 A | 2/1999 | Curro |
| 5,928,212 A | 7/1999 | Kline et al. |
| 5,941,864 A | 8/1999 | Roe |
| 6,010,491 A | 1/2000 | Roe et al. |
| 6,251,097 B1 | 6/2001 | Kline et al. |
| 6,414,215 B1 | 7/2002 | Roe |
| 6,432,098 B1 | 8/2002 | Kline et al. |
| 6,441,266 B1 | 8/2002 | Dyer et al. |
| 6,482,191 B1 | 11/2002 | Roe et al. |
| 6,573,423 B1 | 6/2003 | Herrlein et al. |
| 7,134,258 B2 | 11/2006 | Kalany et al. |
| 7,338,155 B2 | 3/2008 | Niimi |
| 7,524,049 B2 | 4/2009 | Nakashima |
| 7,992,994 B2 | 8/2011 | Kobayashi et al. |
| 8,100,253 B2 | 1/2012 | Walsh |
| 2002/0055430 A1 | 5/2002 | Coenen et al. |
| 2004/0162536 A1 | 8/2004 | Becker et al. |
| 2004/0167486 A1 | 8/2004 | Busam et al. |
| 2010/0300309 A1 | 12/2010 | Schneider |
| 2014/0063085 A1* | 3/2014 | Warner et al. ............... 347/4 |

FOREIGN PATENT DOCUMENTS

| | | |
|---|---|---|
| WO | WO 94/14395 | 7/1994 |
| WO | WO 95/16746 | 6/1995 |
| WO | WO 2006/015141 | 2/2006 |

* cited by examiner

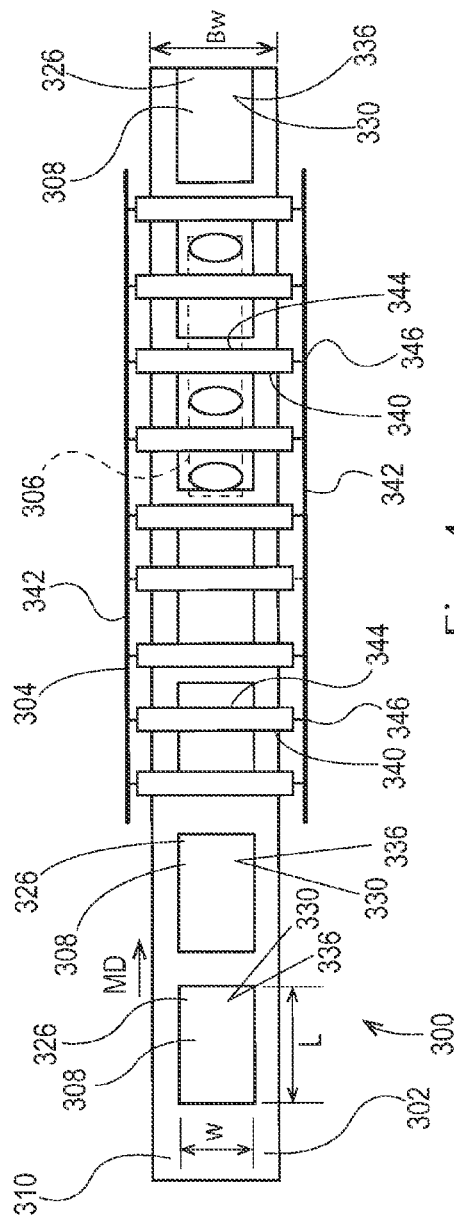
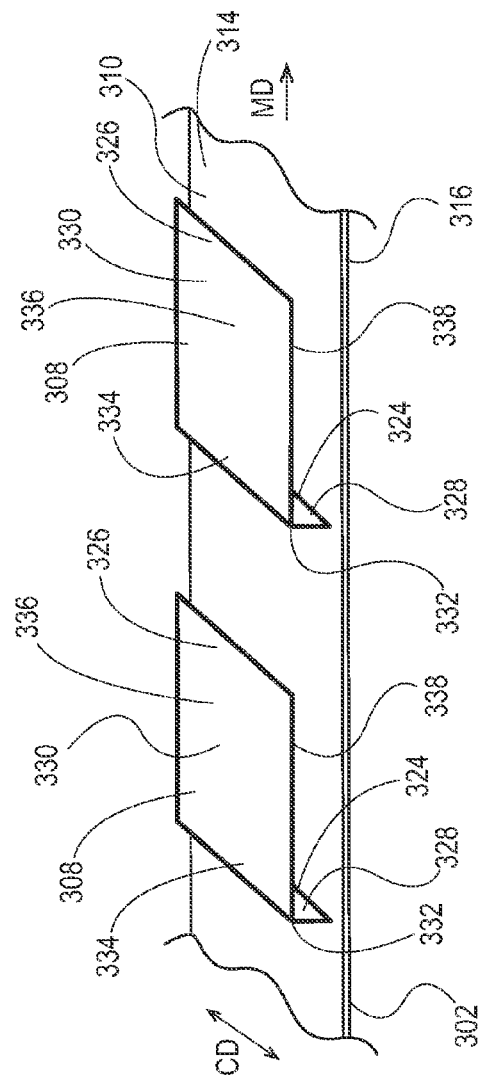

PROCESS AND APPARATUS FOR PRINTING ASSEMBLED ABSORBENT ARTICLES WITH CUSTOM GRAPHICS

CROSS REFERENCE TO RELATED APPLICATION

This application is a continuation of application Ser. No. 13/600,298 filed on Aug. 31, 2012, now U.S. Pat. No. 8,876,279, which is incorporated herein by reference.

FIELD OF THE INVENTION

The present disclosure relates to apparatuses and methods for producing absorbent products, and more particularly, methods for printing graphics on assembled, discrete absorbent articles.

BACKGROUND OF THE INVENTION

Along an assembly line, diapers and various types of other disposable absorbent articles may be assembled by adding components to and otherwise modifying advancing, continuous webs of material. Webs of material and component parts used to manufacture diapers may include: backsheets, topsheets, absorbent cores, front and/or back ears, fastener components, and various types of elastic webs and components such as leg elastics, barrier leg cuff elastics, and waist elastics. In some processes, graphics are printed on individual components and/or continuous webs of material used to assemble the absorbent articles.

Some consumers may prefer purchasing absorbent articles, such as diapers, having a number of different graphic designs printed thereon and provided in a single package. Further, some consumers may prefer purchasing diapers having customized graphics printed thereon. Various methods and apparatuses can be used to print different graphics on an advancing web of material used in the manufacture of absorbent articles. However, such methods and apparatuses may provide for limited numbers of different printed graphics; graphics with relatively low quality print; and/or require relatively low print and/or manufacture speeds. In addition, such methods and apparatuses may also require relatively expensive processes and equipment and may not be very flexible in allowing a user to change the type of graphics to be printed.

As such, there remains a demand to create and supply relatively small quantities of diapers in a single order that are printed with customized/personalized graphics efficiently, while at the same time maintaining a large degree of flexibility to fill large numbers of orders.

SUMMARY OF THE INVENTION

The present disclosure relates to methods and apparatuses for printing graphics on absorbent articles. Printing systems according to the present disclosure may include a carrier apparatus that transports individual absorbent articles past a printing station, which in turn, prints a custom graphic on the absorbent articles. The carrier apparatus may include one or more hook members connected with an endless belt. The printing system may also include a pressing apparatus positioned adjacent to the endless belt. During operation, an absorbent article may be positioned on a hook member, and the endless belt conveys the absorbent article in the machine direction past the printing station. As the absorbent article advances toward the printing station, the pressing apparatus compresses and flattens the absorbent article against the hook member to help provide a relatively flat, smooth and wrinkle-free surface on the absorbent article to be printed. The printing station then prints a graphic on the advancing article.

In one form, a method may be adapted for producing customized absorbent articles, wherein each absorbent article comprises a chassis including a first surface and an opposing second surface, the chassis having a longitudinal axis and a lateral axis, a first end region longitudinally opposed to a second end region, and a central region longitudinally intermediate of the first and second end regions. The method includes the steps of: providing a carrier including an endless belt and a hook member, the hook member including a base member connected with a support member, the support member including a first surface and an opposing second surface, wherein the base member is connected with the endless belt and wherein the support member defines a distal end portion; placing the chassis of an absorbent article on the hook member such that the first surface of the first end region is in a facing relationship with the first surface of the support member, the distal end portion of the support member is adjacent to the central region, and the second end region is positioned between the second surface of the support member and the endless belt; advancing the hook member and the absorbent article in a machine direction; pressing the advancing absorbent article against the first surface of the support member; printing a graphic on the second surface of the advancing absorbent article; and removing the absorbent article from the hook member.

In another form, an apparatus for printing graphics onto absorbent articles includes: an ink jet printing device; an endless belt extending in a machine direction adjacent to the ink jet printing device, the endless belt including a first surface and an opposing second surface; a hook member including: a base member connected with the endless belt; a support member connected with the base member and extending in the machine direction from the base member to a distal end portion, the support member including a first surface and an opposing second surface, wherein the second surface of the support member faces the first surface of the endless belt; a plurality of rollers, each roller having an outer circumferential surface and adapted to rotate about an axis of rotation extending in a cross direction, wherein the rollers are spaced apart from each other along the machine direction with the outer circumferential surfaces adjacent the first surface of the endless belt.

In yet another form, a method may be adapted for producing customized diapers, wherein each diaper comprises a chassis including a first surface and an opposing second surface, the chassis having a longitudinal axis and a lateral axis, a first waist region longitudinally opposed to a second waist region, and a crotch region longitudinally intermediate of the first and second waist regions. The method includes the steps of: receiving an order for diapers having customized graphics printed thereon; programming a printer to print the customized graphics; advancing a hook member in a machine direction, the hook member having a support member defining a distal end portion; positioning the diaper on the hook member such that chassis is folded around the support member to place the crotch region adjacent crotch region; pressing the diaper against the support member; printing a graphic on the advancing diaper; and removing the diaper from the hook member.

BRIEF DESCRIPTION OF THE DRAWINGS

FIG. 4 is a schematic top side view of the printing apparatus shown in FIG. 3.

FIG. 5 is a detailed isometric view of a carrier apparatus.

DETAILED DESCRIPTION OF THE INVENTION

Figure 1:
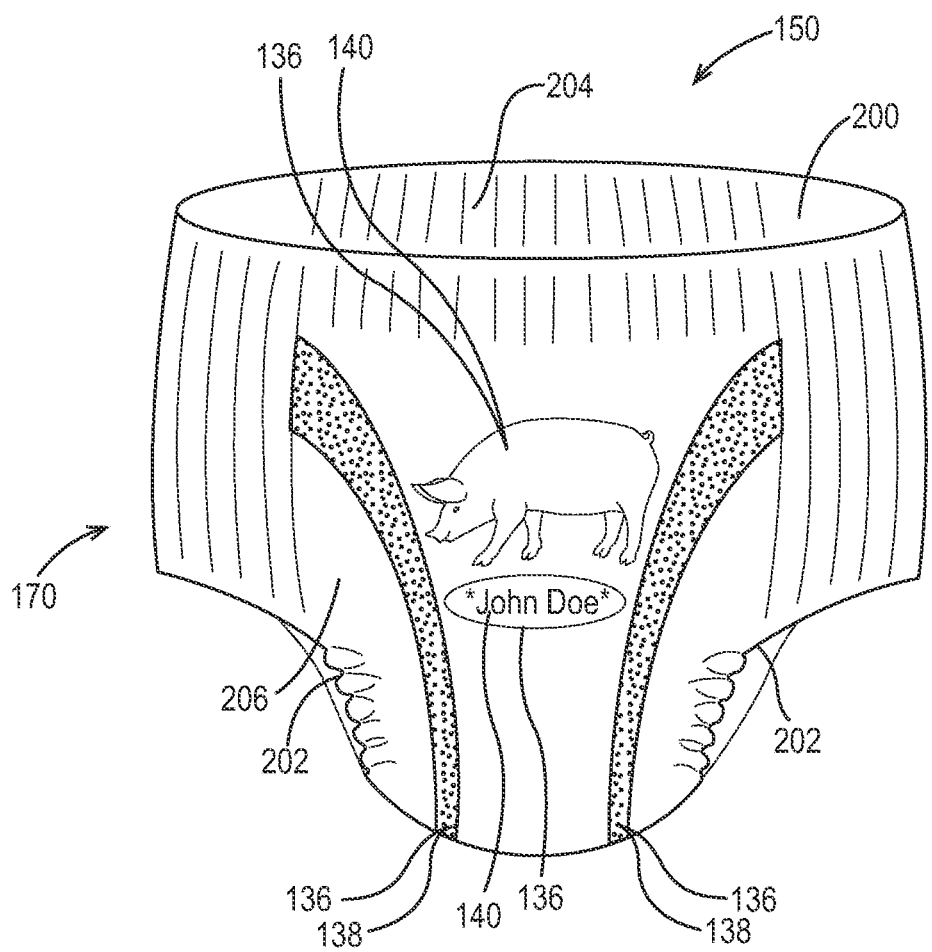
FIG. 1 is a perspective view of an absorbent article.

The following explanation terms may be useful in understanding the present disclosure: "Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a defined woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed.

"Pre-fastened" refers herein to pant diapers manufactured and provided to consumers in a configuration wherein the front waist region and the back waist region are fastened or connected to each other as packaged, prior to being applied to the wearer. As such pant diapers may have a continuous perimeter waist opening and continuous perimeter leg openings designed for infant or adult wearers. As discussed in more detail below, a diaper pant can be preformed by various techniques including, but not limited to, joining together portions of the diaper using refastenable and/or permanent closure members (e.g., seams, heat bonds, pressure welds, adhesives, cohesive bonds, mechanical fasteners, etc.). In addition, pant diapers can be preformed anywhere along the circumference of the waist region (e.g., side fastened or connected, front waist fastened or connected, rear waist fastened or connected).

The term "body facing surface" refers to surfaces of absorbent articles and/or components thereof which face a wearer's body when the absorbent articles are worn, and the term "garment facing surface" refers to surfaces of absorbent articles and/or components thereof that face away from a wearer's body when the absorbent articles are worn. Absorbent articles and components thereof, including the topsheet, backsheet, absorbent core, and any individual materials of their components, have a body facing surface and a garment facing surface.

The term "graphic" refers to images or designs that are constituted by a figure (e.g., a line(s)), a symbol or character, a color difference or transition of at least two colors, or the like. A graphic may include an aesthetic image or design that can provide certain benefit(s) when an absorbent article is viewed. A graphic may be in the form of a photographic image. A graphic may also be in the form of a 1-dimensional (1-D) or 2-dimensional (2-D) bar code or a quick response (QR) bar code. A graphic design is determined by, for example, the color(s) used in the graphic (individual pure ink colors as well as built process colors), the sizes of the entire graphic (or components of the graphic), the positions of the graphic (or components of the graphic), the movements of the graphic (or components of the graphic), the geometrical shapes of the graphic (or components of the graphics), the number of colors in the graphic, the variations of the color combinations in the graphic, the number of graphics printed, the disappearance of color(s) in the graphic, and the contents of text messages in the graphic.

"Different in terms of graphic design" means that graphics are intended to be different when viewed by users or consumers with normal attentions. Thus, two graphics having a graphic difference(s) which are unintentionally caused due to a problem(s) or an error(s) in a manufacture process, for example, are not different from each other in terms of graphic design.

"Standard" or "standardized" refers to graphics, products, and/or articles that have the same aesthetic appearance without intending to be different from each other.

The term "custom" or "customized" refers to graphics, products, and/or articles that are changed to suit a small demographic, region, purchaser, customer, or the like. Custom graphics may be selected from a set of graphics. For example, custom graphics may include animal depictions selected from groups of animals, such as farm animals, sea creatures, birds, and the like. In other examples, custom graphics may include nursery rhymes and the like. In one scenario, custom products or articles may be created by a purchaser of such products or articles wherein the purchaser selects graphics for the articles or products from a set of graphics offered by a manufacturer of such articles or products. Custom graphics may also include "personalized" graphics, which may be graphics created for a particular purchaser. For example, personalized graphics may include a person's name alone or in combination with a design.

Aspects of the present disclosure relates to methods and apparatuses for manufacturing absorbent articles, and more particularly, apparatuses and methods for printing graphics on assembled, discrete individual absorbent articles. It is to be appreciated that various types of graphics may be printed in accordance with the methods and apparatuses herein, such as for example, standardized graphics, custom graphics, and personalized graphics. As discussed in more detail below, printing systems according to the present disclosure may include a carrier apparatus that transports individual absorbent articles in a machine direction past a printing station, which in turn, prints a custom graphic on the absorbent articles. The carrier apparatus may include one or more hook members connected with an endless belt. Each hook member may include a base member connected with the endless belt; and a support member connected with the base member. The support member may extend in the machine direction from the base member to a distal end portion. The printing system may also include a pressing apparatus having a plurality of rollers spaced apart from each other along the machine direction and positioned adjacent the endless belt. During operation, an absorbent article may be positioned on a hook member, and the endless belt conveys the absorbent article in the machine direction past the printing station. As the absorbent article advances toward the printing station, the rollers of the pressing apparatus compress and flatten the absorbent article against the support member to help provide a relatively flat, smooth, wrinkle-free surface on the absorbent article to be printed. A graphic is then printed on the absorbent article while advancing past the printing station. Once printed, the absorbent article may be removed from the hook member.

Figure 2:
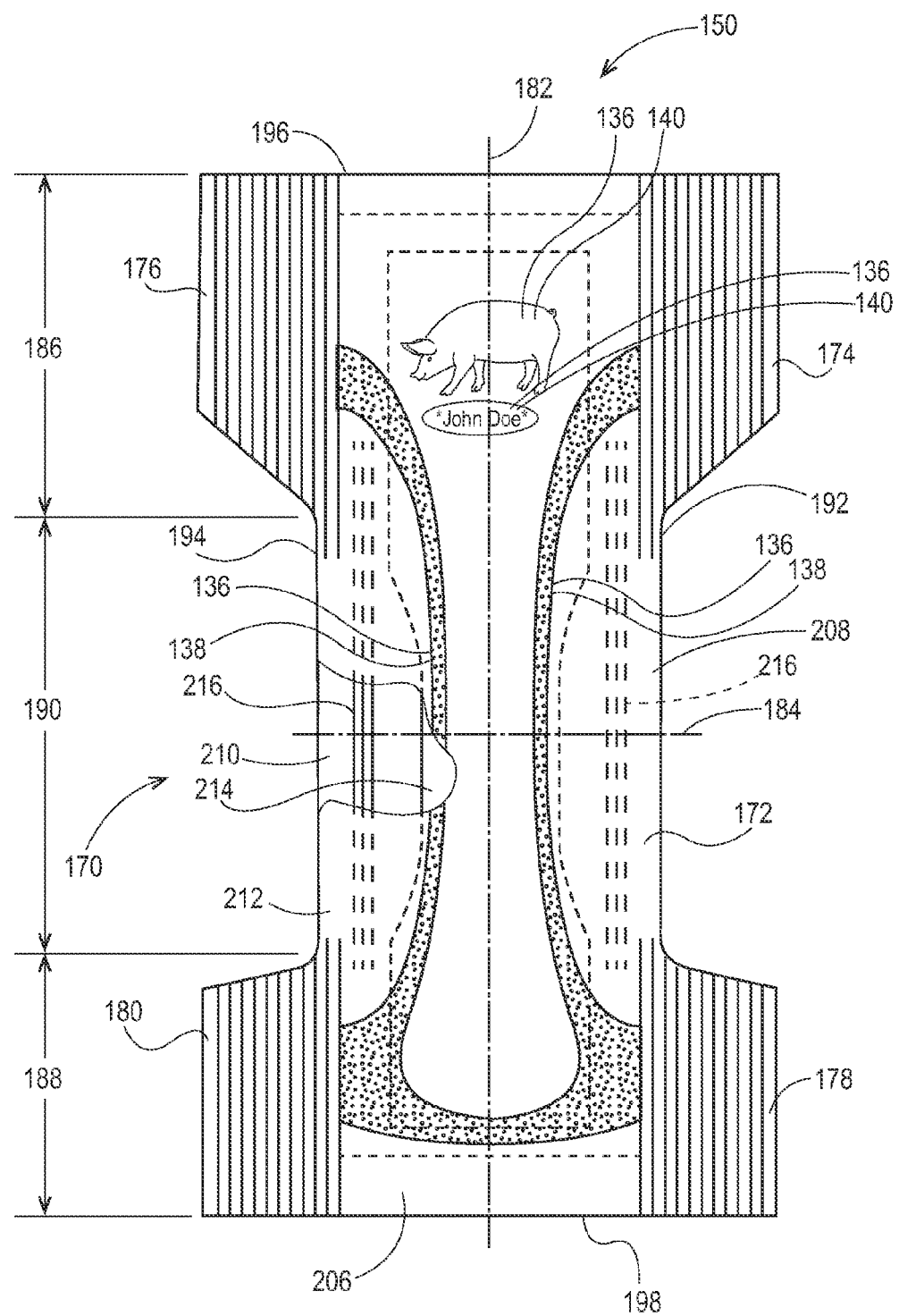
FIG. 2 is a partially cut away plan view of the absorbent article shown in FIG. 1.

It is to be appreciated that although the methods and apparatuses herein may be configured to print various types of products, the methods and apparatuses herein are discussed below in the context of manufacturing absorbent articles. In particular, the methods and apparatuses are discussed in the context of printing diapers during production. For the purposes of a specific illustration, FIGS. 1 and 2 shows one example of a disposable absorbent article 150 in the form of a custom diaper 170 which may be printed in accordance with the apparatuses and methods herein. FIG. 2 is a plan view of the diaper 170 including a chassis 172 shown in a flat, unfolded condition, with the portion of the diaper that faces away from a wearer oriented towards the viewer. A portion of the chassis structure is cut-away in FIG. 2 to more clearly show the construction of and various features that may be included in embodiments of the diaper.

As shown in FIGS. 1 and 2, the diaper 170 includes a 172 chassis having a first ear 174, a second ear 176, a third ear 178, and a fourth ear 180. To provide a frame of reference for the present discussion, the chassis 172 is shown with a longitudinal axis 182 and a lateral axis 184. The chassis 172 is shown as having a first end region 186, a second end region 188, and a central region 190 disposed intermediate the first and second end regions. The first end region may also be referred to as a first waist region 186; the second end region may also be referred to as a second waist region 188; and the central region may also be referred to as a crotch region 190. The periphery of the diaper is defined by a pair of longitudinally extending side edges 192, 194; a first outer edge 196 extending laterally adjacent the first waist region 186; and a second outer edge 198 extending laterally adjacent the second waist region 188. As shown in FIG. 1, the diaper 170 has a waist opening 200 and two leg openings 202. The diaper 170 may also be provided in the form of a pant-type diaper or may alternatively be provided with a re-closable fastening system, which may include fastener elements in various locations to help secure the diaper in position on the wearer. For example, fastener elements may be located on the ears and may be adapted to releasably connect with one or more corresponding fastening elements located in the first or second waist regions.

As shown in FIGS. 1 and 2, the chassis includes an inner, body facing surface 204, and an outer, garment facing surface 206. As shown in FIG. 2, the chassis 172 may include an outer covering layer 208 including a topsheet 210 and a backsheet 212. An absorbent core 214 may be disposed between a portion of the topsheet 210 and the backsheet 212. It is to be appreciated that any one or more of the regions of the chassis may be stretchable and may include various types of elastomeric materials and/or laminates. As such, the diaper may be configured to adapt to a specific wearer's anatomy upon application and to maintain coordination with the wearer's anatomy during wear.

Embodiments of the diaper may also include pockets for receiving and containing waste, spacers which provide voids for waste, barriers for limiting the movement of waste in the article, compartments or voids which accept and contain waste materials deposited in the diaper, and the like, or any combinations thereof Examples of pockets and spacers for use in absorbent products are described in U.S. Pat. Nos. 5,514,121; 5,171,236; 5,306,266; 5,397,318; 5,540,671; and PCT Application WO 93/25172; which are all hereby incorporated by reference herein. Examples of compartments or voids are disclosed in U.S. Pat. Nos. 4,968,312; 4,990,147; 5,062,840; 6,482,191; and 5,269,755, which are all hereby incorporated by reference herein. Examples of suitable transverse barriers are described in U.S. Pat. Nos. 5,554,142 and 5,653,703; and PCT Patent Publication WO 94/14395, which are all hereby incorporated by reference herein. All of the above-cited references are hereby incorporated by reference herein. In addition to or in place of the voids, pockets and barriers, described above, embodiments of the absorbent article may also include a waste management element capable of effectively and efficiently accepting, storing and/or immobilizing viscous fluid bodily waste, such as runny feces, such as described in U.S. Pat. No. 6,010,491, which is hereby incorporated by reference herein.

As previously mentioned, the chassis 172 may include the backsheet 212, shown for example, in FIG. 2. In some embodiments, the backsheet is configured to prevent exudates absorbed and contained within the chassis from soiling articles that may contact the diaper, such as bedsheets and undergarments. Some embodiments of the backsheet may be fluid permeable, while other embodiments may be impervious to liquids (e.g., urine) and comprises a thin plastic film. Some backsheet films may include those manufactured by Tredegar Industries Inc. of Terre Haute, Ind. and sold under the trade names X15306, X10962, and X10964. Other backsheet materials may include breathable materials that permit vapors to escape from the diaper while still preventing exudates from passing through the backsheet. Exemplary breathable materials may include materials such as woven webs, nonwoven webs, composite materials such as film-coated nonwoven webs, and microporous films. Suitable breathable composite materials are described in greater detail in PCT Application No. WO 95/16746, published on Jun. 22, 1995 in the name of E. I. DuPont and U.S. Pat. No. 5,865,823, both of which are hereby incorporated by reference herein. Other breathable backsheets including nonwoven webs and apertured formed films are described in U.S. Pat. Nos. 5,571,096 and 6,573,423, which are all hereby incorporated by reference herein.

The backsheet 212 may be formed by only one sheet (or layer) material such as a breathable (or microporous) film material or a non-breathable (or non-microporous) film material. In some embodiments, the backsheet may be formed by two (or more) sheet (or layer) materials which may include a non-breathable (or breathable) film material and a nonwoven outer cover material. In some embodiments, the backsheet may be formed by a laminate of two sheet (or layer) materials joined together, for example, the backsheet may include a non-breathable film material and a nonwoven material which is joined to the garment facing surface of the film material to provide a cloth-like and/or garment-like feel. In accordance with the discussion below, graphics 136 may be printed directly on the backsheet 212. The diaper 170 shown in FIGS. 1 and 2 includes graphics 136 in the form of standard graphics 138 and custom graphics 140. The standard graphics 138 shown may be identical on each diaper that is printed, and are illustrated in the form of a curved line. It is to be appreciated that the illustrated standard graphics 138 are shown as an example, and various different types of graphics may be used. In addition, the custom graphics 140 are shown in the form of a farm animal (e.g., a pig) and a person's name. It is also to be appreciated that the illustrated custom graphics are examples, and can be printed in various other forms. In addition, the custom graphics can be identical or different on each printed diaper.

As with the backsheet 212, graphics 136 may also be printed on the topsheet 210. All or at least a portion of the topsheet may be liquid pervious, permitting liquid to readily penetrate therethrough. As such, the topsheet may be manufactured from a wide range of materials, such as porous foams; reticulated foams; apertured nonwovens or plastic films; or woven or nonwoven webs of natural fibers (e.g., wood or cotton fibers), synthetic fibers (e.g., polyester or polypropylene fibers), or a combination of natural and synthetic fibers. One example of a topsheet including a web of staple length polypropylene fibers is manufactured by Veratec, Inc., a Division of International Paper Company, of Walpole, Mass. under the designation P-8. Examples of formed film topsheets are described in U.S. Pat. Nos. 3,929, 135; 4,324,246; 4,342,314; 4,463,045; and 5,006,394, all of which are hereby incorporated by reference herein. Other topsheets may be made in accordance with U.S. Pat. Nos. 4,609,518 and 4,629,643, both of which are hereby incorporated by reference herein.

In some embodiments, the topsheet is made of a hydrophobic material or is treated to be hydrophobic in order to isolate the wearer's skin from liquids contained in the absorbent core. If the topsheet is made of a hydrophobic material, at least the upper surface of the topsheet may be treated to be hydrophilic so that liquids will transfer through the topsheet more rapidly. The topsheet can be rendered hydrophilic by treating it with a surfactant or by incorporating a surfactant into the topsheet. A more detailed discussion of such a treatment and hydrophilicity is contained in U.S. Pat. Nos. 4,988,344 and 4,988,345, all of which are hereby incorporated by reference herein. A more detailed discussion of some methods for incorporating surfactant in the topsheet can be found in U.S. Statutory Invention Registration No. H1670, which was published on Jul. 1, 1997, in the names of Aziz et al., all of which are hereby incorporated by reference herein. In some embodiments, the topsheet 210 may include an apertured web or film that is hydrophobic. This may be accomplished by eliminating the hydrophilizing treatment step from the production process and/or applying a hydrophobic treatment to the topsheet, such as a polytetrafluoroethylene compound like SCOTCHGUARD or a hydrophobic lotion composition, as described below. A more detailed discussion of various apertured topsheets can be found in U.S. Pat. Nos. 5,342,338; 5,941,864; 6,010,491; and 6,414,215, all of which are hereby incorporated by referenced herein.

The absorbent core 214 may include components such as an acquisition layer and absorbent material that is generally compressible, conformable, non-irritating to the wearer's skin, and capable of absorbing and retaining liquids such as urine and other body exudates. The absorbent core can also be manufactured in a wide variety of sizes and shapes (e.g., rectangular, hourglass, T-shaped, asymmetric, etc.). The absorbent core may also include a wide variety of liquid-absorbent materials commonly used in disposable diapers and other absorbent articles. In one example, the absorbent core includes comminuted wood pulp, which is generally referred to as airfelt. Examples of other absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

It is to be appreciated that the configuration and construction of the absorbent core may be varied (e.g., the absorbent core(s) or other absorbent structure(s) may have varying caliper zones, a hydrophilic gradient, a superabsorbent gradient, or lower average density and lower average basis weight acquisition zones; or may comprise one or more layers or structures). Exemplary absorbent structures are described in U.S. Pat. Nos. 4,610,678; 4,673,402; and 4,834,735; 4,888, 231; 5,137,537; 5,147,345; 5,342,338; 5,260,345; 5,387,207; and 5,650,222, all of which are hereby incorporated by reference herein.

The absorbent core may also have a multiple layered construction. A more detailed discussion of various types of multi-layered absorbent cores can be found in U.S. Pat. Publication Nos. 2004/0162536A1 and 2004/0167486A1; U.S. Pat. Nos. 5,669,894; 6,441,266; 5,562,646; European Pat. No. EP0565606B1; PCT Publication No. WO 2006/015141, which are all hereby incorporated by reference herein. In some embodiments, the absorbent article includes an absorbent core that is stretchable. In such a configuration, the absorbent core may be adapted to extend along with other materials of the chassis in longitudinal and/or lateral directions. The absorbent core can also be connected with the other components of the chassis various ways. For example, the diaper may include a "floating core" configuration or a "bucket" configuration wherein the diaper includes an anchoring system that can be configured to collect forces tending to move the article on the wearer. Such an anchoring system can also be configured to anchor itself to a body of a wearer by contacting various parts of the body. In this way, the anchoring system can balance the collected moving forces with holding forces obtained from the anchoring. By balancing the collected moving forces with the obtained holding forces, the anchoring system can at least assist in holding the disposable wearable absorbent article in place on a wearer.

The diapers according to the present disclosure can also include other features such as elastically extensible side panels. The side panels may be joined at seams to form the waist opening and the leg openings. The diapers may also includes leg elastics 216, such as shown in FIG. 2, and an elastic waist region to enhance the fits around the legs and waist of the wearer. Example leg elastic and leg cuff embodiments are disclosed in, for example, U.S. Pat. Nos. 4,695,278 and 4,795,454.

In addition to the backsheet and topsheet, graphics may also be printed on other components used to construct the fastening elements on the diaper, such as for example, a landing zone. Depending on the particular configuration, it is to be appreciated that various types of fastening elements may be used with the diaper. In one example, the fastening elements include hook & loop fasteners, such as those available from 3M or Velcro Industries. In other examples, the fastening elements include adhesives and/or tape tabs, while others are configured as a macrofastener or hook (e.g., a MACRO or "button-like" fastener). Some exemplary fastening elements and systems are disclosed in U.S. Pat. Nos. 3,848,594; 4,662,875; 4,846,815; 4,894,060; 4,946,527; 5,151,092; and 5,221,274, which are all hereby incorporated by reference herein. Additional examples of fasteners and/or fastening elements are discussed in U.S. Pat. Nos. 6,482,191; 6,251,097; and 6,432,098, which are all hereby incorporated by reference herein. Other fastening systems are described in more detail in U.S. Pat. Nos. 5,595,567; 5,624,427; 5,735,840; and 5,928,212, which are all hereby incorporated by reference herein. The fastening system may also provide a means for holding the article in a disposal configuration as disclosed in U.S. Pat. No. 4,963,140, which is hereby incorporated by reference herein.

Components of the disposable absorbent article (i.e., diaper, disposable pant, adult incontinence article, sanitary napkin, pantiliner, etc.) described in this specification can at least partially be comprised of bio-sourced content as described in US 2007/0219521A1 Hird et al published on Sep. 20, 2007, US 2011/0139658A1 Hird et al published on Jun. 16, 2011, US 2011/0139657A1 Hird et al published on Jun. 16, 2011, US 2011/0152812A1 Hird et al published on Jun. 23, 2011, US 2011/0139662A1 Hird et al published on Jun. 16, 2011, and US 2011/0139659A1 Hird et al published on Jun. 16, 2011. These components include, but are not limited to, topsheet nonwovens, backsheet films, backsheet nonwovens, side panel nonwovens, barrier leg cuff nonwovens, super absorbent, nonwoven acquisition layers, core wrap nonwovens, adhesives, fastener hooks, and fastener landing zone nonwovens and film bases.

In at least one exemplary configuration, a disposable absorbent article component comprises a bio-based content value from about 10% to about 100% using ASTM D6866-10, method B, in another embodiment, from about 25% to about 75%, and in yet another embodiment, from about 50% to about 60% using ASTM D6866-10, method B.

In order to apply the methodology of ASTM D6866-10 to determine the bio-based content of any disposable absorbent article component, a representative sample of the disposable absorbent article component must be obtained for testing. In at least one embodiment, the disposable absorbent article component can be ground into particulates less than about 20 mesh using known grinding methods (e.g., Wiley® mill), and a representative sample of suitable mass taken from the randomly mixed particles.

Figure 3:
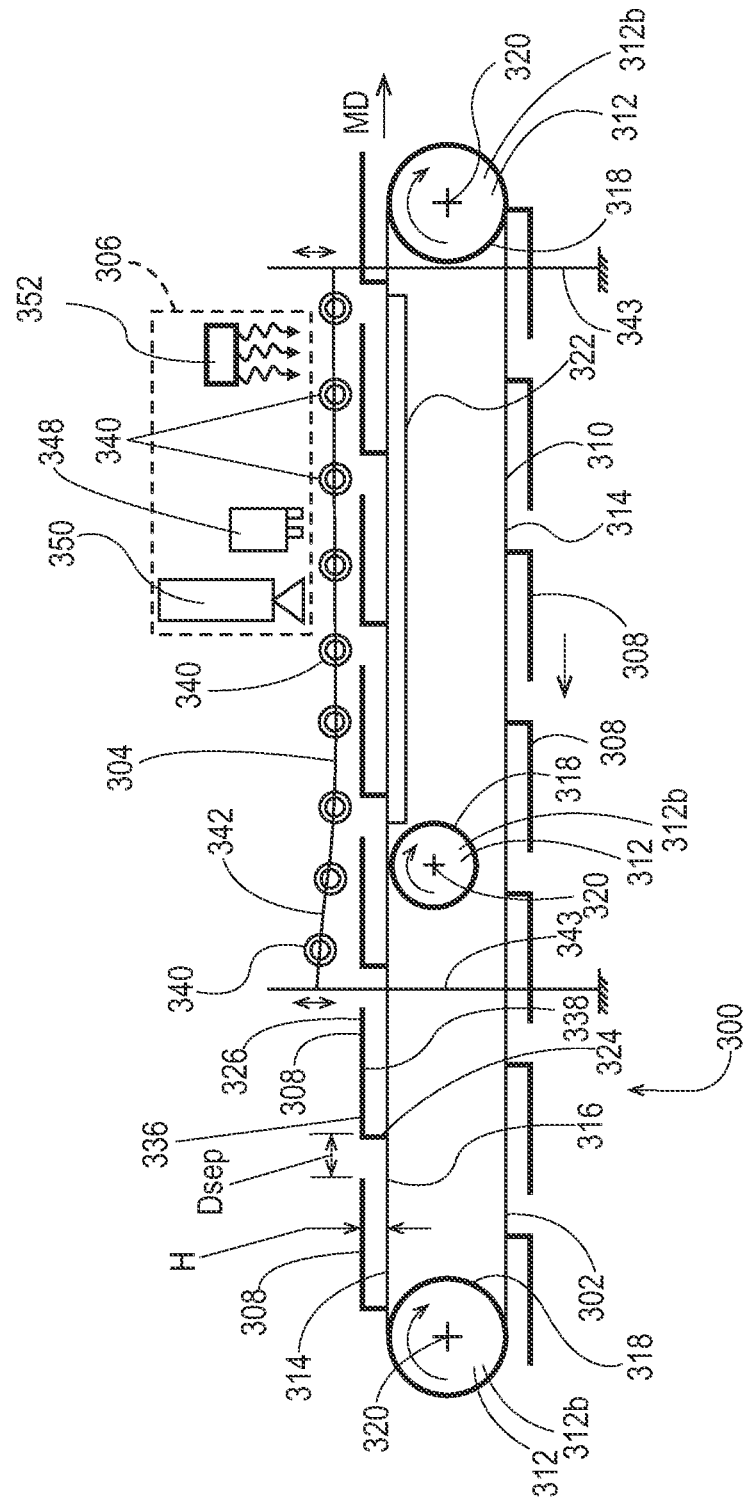
FIG. 3 is a schematic right side view of a printing apparatus.

As previously mentioned, apparatuses and methods according to the present disclosure may be configured for printing graphics on assembled, discrete individual absorbent articles. FIGS. 3 to 5 show an example printing apparatus 300 adapted to print graphics 136 on fully assembled, discrete, individual diapers 170. In one scenario, fully assembled diapers 170 may be removed from an assembly line and/or a package and manually placed on the printing apparatus 300. In turn, the printing apparatus may be configured to print one more graphics 136, such as standard graphics 138 and/or custom graphics 140, on the diapers 170. The printing apparatus 300 may include a carrier apparatus 302, a pressing apparatus 304, and a printing station 306. As discussed in more detail below, the carrier apparatus 302 may convey diapers 170 in a machine direction MD past the printing station 306, which in turn, prints a graphic 136 on the diaper 170. As the diapers move in the machine direction MD, the pressing apparatus 304 compresses and flattens portions of the diapers 170 against the carrier apparatus 302 to help provide a relatively smooth, flat surface on the diapers 170 to be printed. The diapers 170 may be removed from the carrier apparatus 302 after being printed.

Figure 6:
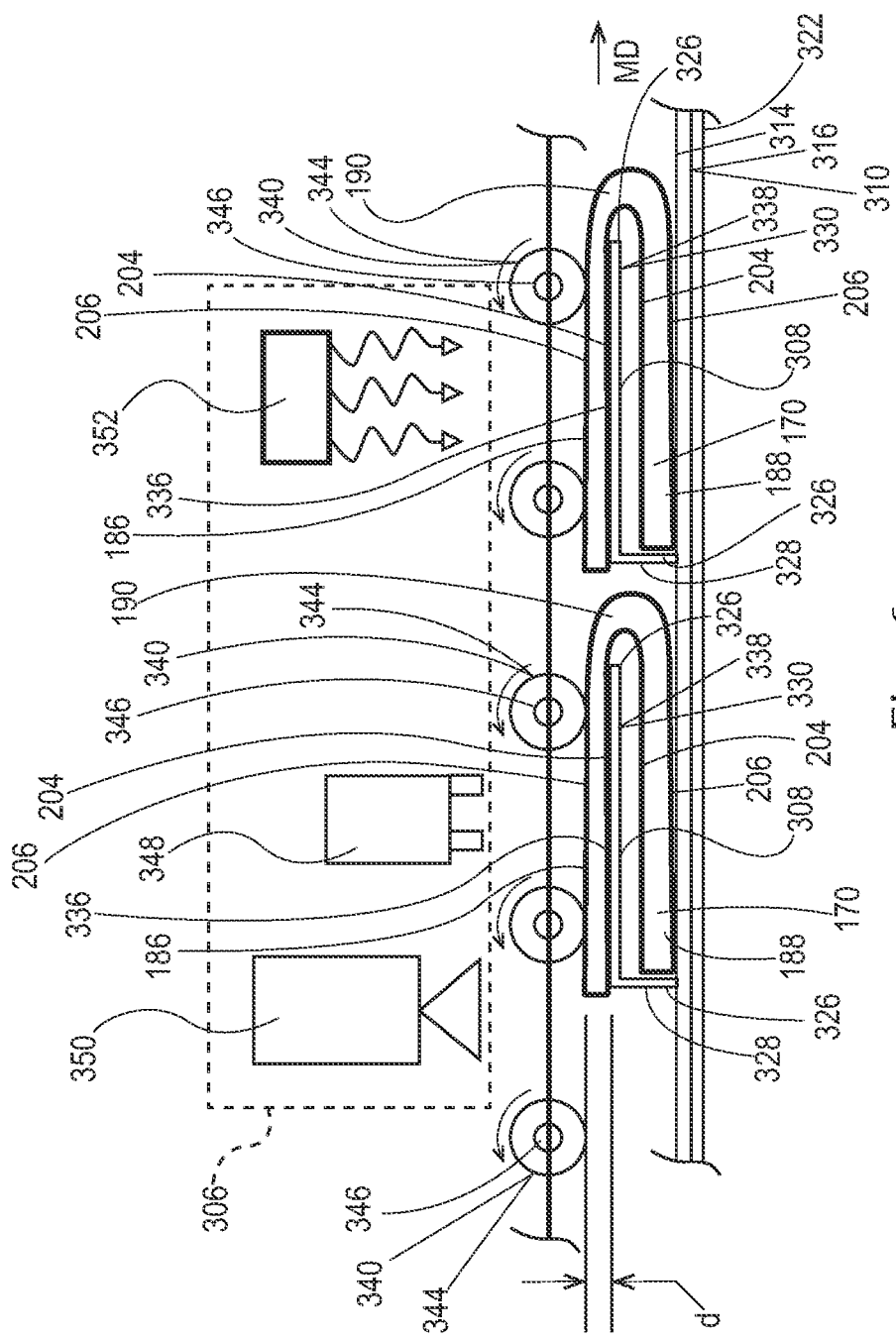
FIG. 6 is a detailed side view of an absorbent article positioned on a printing apparatus.

With continued reference to FIGS. 3 to 5, the carrier apparatus 302 may include one more hook members 308 connected with an endless belt 310 surrounding a plurality or rollers 312. The conveyor rollers 312 may include a drive roller 312a and one or more idler rollers 312b. As discussed in more detail below, diapers 170 may be positioned on the hook members 308, and the endless belt 310 conveys the hook members 308 and diapers 170 positioned thereon in the machine direction MD past the printing station 306. As shown in FIGS. 3 to 5, the endless belt 308 may include a first surface 314 and an opposing second surface 316. Each conveyor roller 312 may each include an outer circumferential surface 318 and may be adapted to rotate about an axis of rotation 320. The second surface 316 of the endless belt 310 may be positioned in contact with the outer circumferential surfaces 318 of the conveyor rollers 312. As shown in FIG. 6, the carrier apparatus 302 may also include a skid plate 322 to help support the endless belt 310 in a region adjacent the print station 306. More particularly, the skid plate 322 may extend in the machine direction MD and the cross direction CD and may be in direct contact with the second surface 316 of the endless belt 310. As such, the skid plate 322 may help prevent and/or reduce deflection of the endless belt 310 away from the printing station 306 while the diapers 170 positioned on hook members 308 advance in the machine direction MD past the printing station 306. It is to be appreciated the printing apparatus 300 may be configured the hook members 308 and diapers 170 positioned thereon at various speeds. For example, in some configurations, the hook members 308 may advance at speeds from about 0.365 to about 1.25 meters per second. In some configurations, the speed may be higher than 1.25 meters per second. It is also to be appreciated that the endless belt may define various different widths, $B_w$, in the cross direction CD. For example, in some configurations, the width, $B_w$, may be about 152.4 mm.

As shown in FIGS. 3 to 5, each hook member 308 may include a proximal end portion 324 connected with the first surface 314 of the endless belt 310. In some configurations, the hook member 308 may include a base member 328 connected with a support member 330. It is to be appreciated that the base member 328 and the support member 330 may be configured as separate parts connected with the each other or may be integrally formed together as a single piece. As shown in FIG. 5, the base member 328 may extend from the proximal end portion 324 to a second end portion 332 that is connected with a first end portion 334 of the support member 330. From the first end portion 334, the support member 330 extends to the distal end portion 326. The support member 330 may include a first surface 336 and an opposing second surface 338 that define a planar shape having a cross directional width, W, and a machine direction length, L. In addition, adjacent hook members 330 may be separated from each other by a distance, $D_{sep}$. It is to be appreciated that the apparatus may be configured with various different widths, W; lengths, L, and separation distances, $D_{sep}$. For example, in some configurations, the length L may be about 230 mm and the separation distance $D_{sep}$ may be about 70 mm. The second surface 338 of the support member 330 may be in a facing relationship with the first surface 314 of the endless belt 310. As shown in FIGS. 3 to 5, the hook member 308 may be connected with the endless belt 310 such that the base member 328 extends away from the first surface 314 of the endless belt 310 and the support member 330 may extend in the machine direction MD to the distal end portion 326. As such, the second surface 338 of the support member 330 may be separated by a distance, H, from the first surface 314 of the endless belt 310. It is to be appreciated that the hook members 308 may be connected with the endless belt in various ways, such as for example, adhesives, welding, and/or fasteners. In some embodiments, the hook members may be formed integrally with the endless belt.

As previously mentioned, the diapers 170 may be positioned on the hook members 308 before being conveyed by the endless belt 310 past the printing station 306. FIG. 6 shows a detailed side view of two diapers 170 positioned on hook members 308. More particularly, the diapers 170 may be positioned such that the outer, garment facing surface 206 of the first waist region 186 is in a facing relationship with the printing station 306. And the inner, body facing surface 204 of the first waist region 186 of the diaper 170 is in a facing relationship and in direct contact with the first surface 336 of the support member 330. The diaper 170 may be folded around the support member 330 such that the distal end portion 326 of the support member is adjacent to the inner, body facing surface 204 of the crotch region 190 of the diaper 170. In addition, the inner, body facing surface 204 of the second waist region 188 may be in a facing relationship with the second surface 338 of the support member 330, and the outer, garment facing surface 206 of the second waist region 188 is in a facing relationship with the first surface 314 of the endless belt 310.

It is to be appreciated the diaper 170 can be positioned on the hook member 308 in various other orientations than what is shown and described with respect to FIG. 6. For example, the diaper 170 may be positioned on the hook members such that the second waist region 188 is located between the first surface 336 of the support member 330 and the printing station 306. In another orientation, the outer, garment facing surface 206 of the diaper 170 may be positioned in a facing relationship with the first surface 336 and the second surface 338 of the support member 330.

As previously mentioned, the printing apparatus 300 may also include a pressing apparatus 304 that compresses the diaper 170 against the hook member 308 as the diaper is conveyed in the machine direction MD past the printing station 306. As shown in FIGS. 3, 4, and 6, the pressing apparatus 304 may include a plurality of rollers 340 rotatably connected with a frame 342. Each roller 340 may include a cylindrically-shaped outer circumferential surface 344. The rollers 340 may be spaced apart from each other along the machine direction MD and each roller 340 may be adapted to rotate about an axis of rotation 346 extending in a cross direction CD. The rollers 340 may be supported adjacent the first surface 314 of the endless belt 310 such that the hook members 308 are advanced in the machine direction between the endless belt 310 and the outer circumferential surfaces 344 of the rollers 340. The frame 342 may support the rollers 340 to as to define a minimum distance, d, between the outer circumferential surfaces 344 of the rollers 340 and the first surfaces 326 of support members 330. In some configurations, the distance, d, may be the same distance between all or some rollers 340 and support members 330. In some configurations, the distance, d, between rollers 340 and the support members 330 may progressively decrease along the machine direction MD. As shown in FIG. 6, as a diaper 170 positioned on a hook member 308 advances in the machine direction MD, the outer circumferential surfaces 344 of the rollers 340 press the diaper against first surface 336 of the support member 336. As such, the rollers 340 compress and help flatten the diaper 170 against the support member to provide a relatively smooth, flat surface in preparation for printing at the printing station 306. It is to be appreciated that some pressing mechanisms may be configured with an endless belt surrounding the rollers 340. In some configurations, the pressing mechanism may comprise a smooth, stationary skid plate.

In some configurations, the printing apparatus 300 may be configured with one or more various features that allow the distance, d, between the outer circumferential surfaces 344 of the rollers 340 and the first surfaces 326 of support members 330 to be automatically or manually adjusted. For example, the frame 342 may include adjustable support members 343 adapted to allow the position of the frame 342 relative to the endless belt 310 and/or hook members 308 to be adjusted. In some configurations, the positions of the hook members 308 relative to the endless belt 310 may be adjustable. In some configurations, the positions of the support members 330 relative to the base members 328 may be adjustable.

As previously mentioned, the endless belt 310 advances the hook members 308 and diapers 170 positioned thereon in the machine direction MD past the printing station 306, which in turn, prints graphics 136 on the diapers 170. It is to be appreciated that the printing station 306 may be configured in various ways and may include various types of printing accessories. For example, in some embodiments, the printing station 306 may include a printer 348 in the form of an ink-jet printer. Ink-jet printing is a non-impact dot-matrix printing technology in which droplets of ink are jetted from a small aperture directly to a specified position on a media to create a graphic. Two examples of inkjet technologies include thermal bubble or bubble jet and piezoelectric. Thermal bubble uses heat to apply to the ink, while piezoelectric uses a crystal and an electric charge to apply the ink. In some configurations, the printing station 306 may include a corona treater 350, which may be positioned upstream of the printer 348. The corona treater 350 may be configured to increase the surface energy of the surface of the diaper 170 to be printed. In some embodiments, the corona treater 350 may be configured to increase the surface energy of the outer surface of a diaper to about 42 dynes/cm. In some configurations, the printing station 306 may also include an ink curing apparatus 352. In some configurations, the ink curing apparatus 352 may be in the form of an ultraviolet (UV) light source 352 that may include one or more ultraviolet (UV) lamps, which may be positioned downstream of the printer 348 to help cure inks deposited onto the diaper 170 from the printer 348 to form the graphics 136. In some configurations, the ink curing apparatus 352 may also include an infrared (IR) dryer light source that may include one or more infrared (IR) lamps, which may be positioned downstream of the printer 348 to help dry water-based or solvent-based inks deposited onto the diaper 170 from the printer 348 to form the graphics 136. In some configurations, the ink curing apparatus 352 may include an electron beam (EB or e-beam) generator that may include one or more e-beam electrodes, which may be positioned downstream of the printer 348 to help cure inks deposited onto the diaper 170 from the printer 348 to form the graphics 136.

In some configurations, the printing station 306 may be adapted to interface with a computer that allows an operator to manually program the type of graphics to be printed. For example, the printing station 306 may be configured with various features, such as available on the XD070 Multi-Color Industrial Ink Jet unit available from Pad Print Machinery of Vermont. In some configurations, the printing station 306 may be configured to interface with other computerized systems and/or networks that may automatically program or command the printing station 306 to print various graphics based on various input, such as sales orders from customers.

To provide additional context to the above discussion, the following provides a description of an example implementation of the printing methods and apparatuses herein with reference to various elements identified in FIGS. 1 to 6. In a method of operation, one or more orders for diapers having graphics 136 may be received. In response to such orders, the printing station 306 may be programmed to print the graphics 136 specified in the order or orders, such as standard graphics 138 and/or customized graphics 140. In one scenario, an order may request personalized graphics to be printed on diapers 170 available for purchase in various packaged quantities offered by a diaper manufacturer. As such, fully assembled diapers may be removed from such a package, printed with the requested graphics, repackaged, and provided to a consumer in fulfillment of the order.

With continued reference to FIGS. 1 to 6, upon receipt of an order for printed diapers, fully assembled or completely manufactured, individual diapers 170 may be taken from an assembly line or unpacked from a package and positioned on the carrier apparatus 302. More particularly, each diaper 170 may be positioned on a respective hook member 308. For example, an order may specify custom graphics 140, such as personalized graphics, to be printed on the backsheets 212 of diapers 170. An operator may place individual diapers 170 on the hook members 308 such that the inner, body facing surface 204 or topsheet 210 of either the first waist region 186 or second waist region 188 of the diaper 170 is in a facing relationship with the first surface 336 of the support member 330. The diaper 170 may be folded around the support member 330 such that the crotch portion 190 is adjacent the distal end portion 326 of the hook member 308. And the opposing waist region of the diaper 170 may be positioned between the second surface 338 of the support member 330 and the first surface 314 of the endless belt 310.

Once the diaper 170 is positioned on the hook member 308, the endless belt 310 may advance the diaper 170 in the machine direction MD toward the printing station 306. While advancing in the machine direction MD, the rollers 340 contact the outer, garment facing surface 206 or backsheet 212 of the diaper 170 and press the diaper against the first surface 336 of the support member 330. The compression of the diapers 170 between the support member 330 and the rollers 340 helps to flatten and smooth out a portion of the backsheet 212 to be printed at the printing station 306. As the diaper 170 continues advance in the machine direction MD, the corona treater 350 may act on the backsheet 212 to increase the surface energy of the backsheet material. From the corona treater 350, the diaper 170 advances in the machine direction MD past the printer 348 to be printed with the graphics 136 on the backsheet 212 in accordance with the received order. From the printer 348, the diaper 170 may advance in the machine direction MD past the ink curing apparatus 352 to cure the ink deposited on the backsheet 212 from the printer 348 to create the graphic 136. An operator may then remove the diaper 170 from the hook member 308 and packaged to be provided to a customer in fulfillment of the received order.

As discussed above, diapers may be positioned on hook members in various ways so as to print graphics on various components of the diapers. For example, the diapers may be positioned on the hook members to print the topsheets, backsheets, and/or fastening components. The diapers may also be advanced through the printing apparatus more than once in order to print graphics on additional locations and/or components. For example, diapers may be advanced through the printing apparatus to print graphics on first and second waist regions and/or both the topsheets and backsheets.

Although the present disclosure is provided in the context of manufacturing absorbent articles, and diapers in particular, it is to be appreciated that the systems and methods disclosed herein may be applied to the manufacture of various types of articles and products, individually or wound roll, involving various different types of substrates and/or components. Examples of other products may include absorbent articles for inanimate surfaces such as consumer products whose primary function is to absorb and retain soils and wastes that may be solid or liquid and which are removed from inanimate surfaces such as floors, objects, furniture and the like. Non-limiting examples of absorbent articles for inanimate surfaces include dusting sheets, pre-moistened wipes or pads, paper towels, dryer sheets. Additional examples of products include absorbent articles for animate surfaces whose primary function is to absorb and contain body exudates and, more specifically, devices which are placed against or in proximity to the body of the user to absorb and contain the various exudates discharged from the body. Non-limiting examples of incontinent absorbent articles include diapers, adult incontinence briefs and undergarments, feminine hygiene articles such as sanitary pads, panty liners, absorbent inserts, and the like, toilet paper, tissue paper, disposable kitchen towels, disposable napkins, facial wipes or clothes, toilet training wipes. Still other examples of products include packaging components and substrates and/or containers.

It is also to be appreciated that the printing apparatuses and methods disclosed herein may be adapted to include various additional features and configurations. For example, the endless belt and/or hook members may be configured to operate in conjunction with vacuum systems that help hold the absorbent articles in position during printing. In another example, a vacuum system may be utilized to hold the absorbent articles in position without the need for hook members. In another example, as opposed to having an endless belt, the carrier apparatus may be configured with one or more linear motors to advance the hook members past the print device. Such linear motor technology and carrier configurations that could be adapted to advance the hook members are disclosed in U.S. Pat. No. 7,134,258 and 8,100,253. In yet other configurations, the printing apparatus may be configured such that the diaper is held stationary and the printing station moves adjacent the diapers while printing the graphics. The printing apparatuses herein may also be adapted to include vision systems utilizing cameras that may verify printing quality, color authenticity, color intensity, text/graphic location, and printing defects. Systems that count the number of printed diapers and automatically performs packing operations of such printed diapers may also be adapted to work in conjunction with the printing apparatuses and methods herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for producing customized absorbent articles, each absorbent article comprising a chassis including a first surface and an opposing second surface, the chassis having a longitudinal axis and a lateral axis, a first end region longitudinally opposed to a second end region, and a central region longitudinally intermediate of the first and second end regions, the method comprising the steps of:
   providing a carrier comprising an endless belt;
   placing a chassis of an absorbent article on the endless belt;
   advancing the endless belt and the absorbent article in a machine direction;
   pressing the advancing absorbent article against the endless belt;
   increasing the surface energy of the second surface of the chassis;
   printing a graphic on the second surface of the advancing absorbent article; and
   removing the absorbent article from the endless belt.

2. The method of claim 1, wherein the compressing step further comprises advancing the first end region in the machine direction between a plurality of rollers and the endless belt.

3. The method of claim 1, wherein the first end region is a first waist region, the second end region is a second waist region, and the central region is a crotch region.

4. The method of claim 3, wherein the first waist region comprises a front waist region.

5. The method of claim 3, wherein the second surface of the chassis comprises a garment facing surface.

6. The method of claim 1, wherein the second surface of the chassis is defined by a backsheet.

7. The method of claim 1, wherein the step of increasing the surface energy further comprises advancing the chassis in the machine direction past a corona treater.

8. The method of claim 1, wherein the step of printing further comprising depositing ink onto the second surface of the chassis from an ink jet printer.

9. The method of claim 8, further comprising the step of curing the ink.

10. The method of claim 9, wherein the step of curing further comprises advancing the chassis past an ink curing apparatus selected from the group of consisting of: an ultra violet light source and an electron beam generator.

* * * * *